United States Patent [19]

Imamura et al.

[11] 3,950,437

[45] Apr. 13, 1976

[54] METHOD FOR MANUFACTURE OF DIHYDRIC PHENOLS

[75] Inventors: Juichi Imamura, Chofu; Moriyasu Ando, Koganei; Kazuo Sasaki, Kuwana; Takumi Iio, Mie, all of Japan

[73] Assignee: Oxirane Chemical Co., Tokyo, Japan

[22] Filed: Dec. 14, 1973

[21] Appl. No.: 424,687

[30] Foreign Application Priority Data

Dec. 25, 1972 Japan.............................. 47-129301
Feb. 14, 1973 Japan.............................. 48-18147
May 10, 1973 Japan.............................. 48-51940
Aug. 28, 1973 Japan.............................. 48-95750
Sept. 3, 1973 Japan.............................. 48-99067

[52] U.S. Cl. ......... 260/621 G; 260/625; 260/613 D
[51] Int. Cl.$^2$ ......................................... C07C 39/08
[58] Field of Search............. 260/621 G, 621 R, 625

[56] References Cited
UNITED STATES PATENTS

| | | |
|---|---|---|
| 2,395,638 | 2/1946 | Milas .............................. 260/621 G |
| 3,514,490 | 5/1970 | Marlard .......................... 260/621 G |
| 3,652,597 | 3/1972 | Bader et al. ..................... 260/621 G |
| 3,692,842 | 9/1972 | Massie ........................... 260/624 R |
| 3,849,502 | 11/1974 | Bourdin .......................... 260/621 G |

Primary Examiner—James O. Thomas, Jr.
Assistant Examiner—W. B. Lone
Attorney, Agent, or Firm—Oblon, Fisher, Spivak, McClelland & Maier

[57] ABSTRACT

Dihydric phenols are produced preferentially in high yields by having monohydric phenols or phenyl ethers oxidized by an organic peracid using, as a catalyst, at least one member selected from the group consisting of peracid stabilizers, polycarboxylic acids containing N or OH and possessed of a structure from which heavy metal ion-chelating property can theoretically be assumed, magnesium salts, sodium salts and potassium salts thereof, sodium salt, potassium salt and lower alkyl esters of phosphoric acid, and sodium salt and lower alkyl esters of pyrophosphoric acid.

6 Claims, No Drawings

METHOD FOR MANUFACTURE OF DIHYDRIC PHENOLS

BACKGROUND OF THE INVENTION:

This invention relates to a method for the manufacture of dihydric phenols in high yields by oxidizing monohydric phenols represented by the generic formula:

(wherein, R is one member selected from the group consisting of H and alkyls having 1 – 12 carbon atoms) and phenyl ethers represented by the generic formula:

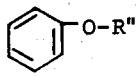

(wherein, R'' is one member selected from the group consisting of alkyls and aryls having 1 – 12 carbon atoms) by an organic peracid in the presence of a catalyst.

In oxidizing benzene rings for thereby introducing the hydroxyl group therein, there have already been suggested the following techniques. French Pat. No. 1,479,354, for example, relates to a method for producing pyrocatechol and hydroquinone by the oxidation of phenols. The oxidation is effected by a peracid, with phosphoric acid used as a catalyst in an amount of 1 – 2% by weight based on the phenol. As concerns the treatment following the reaction, since the distillation, if performed in the presence of the acid catalyst, entails degradation of the yield of dihydric phenol, it is necessary that the reaction solution should be neutralized prior to distillation. The yield is as low as 54%. In the oxidation of phenols by peracids, it has already been known that such acid substances as hydrogen fluoride and boric esters besides said phosphoric acid accelerate the oxidation. The addition of such acid substances barely serves to increase the yield to about 65% at most. The addition, at the same time, increases by-products. It is also known to the art that the oxidation of phenyl ethers by peracids leads to formation of monoethers of dihydroxy phenols. It is further known that the oxidation is effected by highly reactive organic peracids and that the presence of boron trifluoride or some other similar catalyst is effective in further heightening the reactivity of said organic peracids. (J. D. McClure, J. Org. Chem., 27, 627 (1962).)

The primary object of this invention is to provide a method for the manufacture of dihydric phenols in unusually high yields by the oxidation of monohydric phenols.

Another object of this invention is to provide a method for the manufacture of dihydric phenols in unusually high yields by the oxidation of phenol ethers.

SUMMARY OF THE INVENTION:

This invention accomplishes the objects mentioned above by oxidizing monohydric phenols represented by the generic formula:

(wherein, R is one member selected from the group consisting of H and alkyls having 1 – 12 carbon atoms) and phenyl ethers represented by the generic formula:

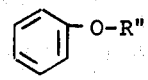

(wherein, R'' is one member selected from the group consisting of alkyls and aryls having 1 – 12 carbon atoms) by an organic period in the presence, as a catalyst, of at least one member selected from the group consisting of peracid stabilizers; polycarboxylic acids containing N and possessed of a structure from which heavy metal ion-chelating property can theoretically be assumed, magnesium salts, sodium salts and potassium salts thereof; polycarboxylic acids containing OH and possessed of a structure from which heavy metal ion-chelating property can theoretically be assumed, magnesium salts and sodium salts thereof; sodium salt, potassium salt and mono and di lower alkyl ester of phosphoric acid; and sodium salt and mono, di and tri lower alkyl ester of pyrophosphoric acid, for thereby producing dihydric phenols in extremely high yields.

Other objects and other characteristic features of the present invention will become apparent from the description given in further detail herein after.

DETAILED DESCRIPTION OF THE INVENTION:

Production of organic peracids on a commercial scale has now become feasible by means of the autoxidation reaction of lower aliphatic aldehydes. As convenient oxidizing agents, the organic peracids thus produced are drawing attention. The inventors pursued various studies in search of a method for producing dihydric phenols by introducing the hydroxyl group into benzene rings by use of these organic peracids. They found that dihydric phenols could be produced in high yields by oxidizing compounds represented by the generic formula:

(wherein, R is one member selected from the group consisting of H and alkyls having 1 – 12 carbon atoms) and compounds represented by the generic formula:

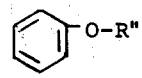

(wherein, R'' is one member selected from the group consisting of alkyls and aryls having 1 – 12 carbon atoms) by organic peracids while using, as a catalyst, at least one member selected from the group of various substances to be described herein below. Of the organic peracids which are usable for this invention, lower aliphatic peracids are invariably effective. Among these effective peracids, peracetic acid, perpropionic acid and perisobutyric acid are particularly suitable for practical use and are capable of producing dihydric phenols in outstanding yields.

Now, a description will be made of the catalyst to be used for the present invention. The substances which can serve as the catalyst are peracid stabilizers, polycarboxylic acids containing N and possessed of a structure from which heavy metal ion-chelating property can theoretically be assumed, magnesium salts, sodium salts and potassium salts thereof; polycarboxylic acids containing OH and possessed of a structure from which heavy metal ion-chelating property can theoretically be assumed, magnesium salts and sodium salts thereof; sodium salt, potassium salt and mono and di lower alkyl ester of phosphoric acid; and sodium salt and mono, di and tri lower alkyl ester pyrophosphoric acid. These substances may be used individually or in the form of a mixture of two or more members.

Examples of the peracid stabilizers mentioned above include pyridine-2,6-dimethanol, 8-oxyquinoline, dioctyl-dihydrogenpyrophosphate, and phosphorus-containing acid esters of the formulas $Na_5R'_5(P_3O_{10})_2$ and $H_5R'_5(P_3O_{10})_2$ (wherein, $R'$ is an alkyl having 4 to 10 carbon atoms).

It has also been found that polycarboxylic acids such as iminodiacetic acid, nitrylotriacetic acid, ethylenediaminotetraacetic acid, 1,2-cyclohexandiamine tetraacetic acid, diethylenetriamine pentaacetic acid, citric acid and tartaric acid which contain N or OH and possessed of a structure from which heavy metal ion-chelating property can theoretically be assumed, sodium salts, potassium salts and magnesium salts of said acids, monobasic and dibasic sodium salts and potassium salt of phosphoric acid and sodium salt of pyrophosphoric acid function as highly effective catalysts.

Compared with the conventional methods using known catalysts such as, for example, the method involving the use of a phosphoric acid catalyst, the method of this invention can produce dihydric phenols from monohydric phenols and phenyl ethers with excellent selectivity by using only a small amount of a catalyst.

The reason for the pronounced effectiveness of the aforementioned compounds as catalysts will be explained.

Of the aforementioned compuonds, those other than peracid stabilizers also have an ability to stabilize peracids, though to a varying degree. This property of stabilizing peracids is judged to function effectively in the oxidation of said monohydric phenols and phenyl ethers by peracids. The function of the compound as the peracid stabilizer alone cannot offer an adequate reason for its outstanding property as the catalyst. The catalyst is required to be used in a much larger quantity than necessary when the compound is used solely as a peracid stabilizer. Take dioctyl-dihydrogenpyrophosphate, for example. For the purpose of this invention, said ester is required to be used in an amount more than ten times as large as when it is serving as a peracid stabilizer.

Thus, possible existence of some other function is implied.

The catalyst used for the method of this invention is believed to have an additional function to prevent produced dihydric phenols from undergoing further oxidaton, namely, to preclude possible secondary oxidation.

Use of an acid catalyst such as phosphoric acid in the oxidation of phenols by a peracid is already known to the art. In this case, phosphoric acid serving as the catalyst is believed to activate the peracid. However, since the substances usable as catalysts for the method of this invention include many basic substances, said peracid-activating mechanism which has found general acceptance fails to explain the behavior of the catalyst under review. It is known that a phenol in a basic solution undergoes dissociation to give rise to a phenoxy anion and consequently heighten the oxidation velocity. Of the substances usable as the catalysts for this invention, therefore, those which are basic possibly serve, on account of said mechanism involving dissociation, the purpose of enhancing phenols in their capability of being oxidized. The peracid consumption velocity constitutes one criterion for rating the capacity of a given catalyst. This velocity is increased by 10 to 15% when the catalyst is used in the amount which is specified for use with the method of this invention.

The function of the catalyst used for the purpose of this invention has been explained. In the method of this invention, the various substances mentioned above manifest peracid-stabilizing function, phenol-activating function, peracid-activating function, secondary oxidation-preventing function, etc. which synergistically cooperate in the oxidation of monohydric phenols and phenyl ethers into dihydric phenols by an organic peracid with surprisingly high selectivity in high yields.

Referring to the generic formulae representing the monohydric phenols and phenyl ethers subjected to oxidation by the method of this invention, when the substituents denoted therein by $R$ and $R''$ are alkyls and aryls, the numbers of carbon atoms thereof need not be limited. From the practical point of view, however, the carbon atoms of said substituents are limited to the range of 1 – 12.

Now, the process for carrying out this invention will be explained. The organic peracid may be used, if occasion demands, in a state dissolved in an organic solvent. The kind of the organic solvent used therefor is not critical. Lower esters, lower ketones and hydrocarbons may be used as satisfactory solvents individually or in the form of a mixture of two or more members. Particularly desirable organic solvents are methyl acetate, ethyl acetate, acetone, acetic acid, benzene and toluene. Methyl acetate, ethyl acetate, acetone and acetic acid are generally used as solvents in the production of peracids and, therefore, may be put to use in the form of concentrated peracid solutions in the method of this invention. Benzene and toluene are especially advantageous as solvents for higher alkyl phenols.

Desirably the organic peracid may be used in an amount of not more than 1 mol, preferably in the range of from 0.1 to 0.5 mol, per each mol of the monohydric phenol or phenyl ether. If the peracid is used in an amount in excess of 0.5 mol, the dihydric phenol and the monoether thereof to be formed by the oxidation are suffered to undergo secondary oxidation, with the result that the yield of the product aimed at is degraded to an extreme extent. When the amount is less than the lower limit of 0.1 mol, the velocity of the oxidation is lowered so much as to render the operation impractical.

The quantity in which the catalyst is effectively used for the method of the present invention will be explained. As previously described, the effective amount of the catalyst is at least ten times as large as when the catalyst would be employed solely as a stabilizer for the peracid. Though this amount may seem quite large, it is fairly small as compared with that of the oxidation catalyst used for the oxidation of phenols by the conventional method.

To be specific, the quantity of the catalyst to be used is sufficient in the range of from 0.05 to 1% by weight for a monohydric phenol and in the range of from 0.1 to 1% by weight for a phenyl ether respectively as the raw material. Any excess over the upper limit of 1% by weight does not bring about any discernible increase in the effect. Rather, such excess at times can accelerate decomposition of the peracid. No desired effect is accomplished when the quantity is less than the lower limit.

The condition of reaction temperature will be explained.

In order for the reaction to proceed efficiently, it must be carried out under application of heat. Too high a temperature can cause the peracid or the product to undergo decomposition. In the oxidation of monohydric phenols, the temperature must be maintained below 150°C, preferably in the range of from 50° to 100°C. In the oxidation of a phenyl ether, it must be

EXAMPLE 1:

Five-neck flasks having a volume of 500 ml and provided with a stirrer, a reflux condenser, a sampling tube, a test specimen inlet and a thermometer were charged with 94.11g (1.0 mol) of phenol and a different kind of peracid stabilizer as a catalyst shown in Table 1. Each flask was then placed in a constant temperature bath maintained at a temperature indicated in Table 1. Into the flask contents, 7.61g (0.1 mol) of peracetic acid in the form of about 35 weight % acetone solution was added through a micro-feeder over a period of 20 minutes. Within 75 minutes after the start of the addition of this peracetic acid, the product was analyzed by gas chromatography. The results are shown in Table 1. For comparison, results obtained in a reaction carried out in the absence of a catalyst and in another reaction carried out in the presence of phosphoric acid catalyst are shown in the same table.

Table 1

| | Catalyst | | | | |
|---|---|---|---|---|---|
| | Kind | Added amount (% by weight) | Reaction temperature (°C) | Conversion of peracetic acid (%) | Pyrocatechol produced (g) *3 | Hydroquinone produced (g) *3 |
| Comparative | — | | 60 | 82.4 | 3.04(33.4) | 0.67( 8.1) |
| | Phosphoric acid | 2.0 | 60 | 87.6 | 3.09(32.0) | 0.89( 9.2) |
| Present invention | Pyridine-2,6-dimethanol | 0.2 | 60 | 91.1 | 3.25(32.4) | 2.45(24.4) |
| | 8-Oxyquinoline | 1.0 | 60 | 95.6 | 3.65(35.0) | 2.33(22.2) |
| | Dioctyl-dihydrogen-pyrophosphate | 0.1 | 80 | 93.0 | 4.19(40.9) | 2.71(26.5) |
| | Phosphorus-containing acid ester *1 | 0.1 | 100 | 98.3 | 4.70(43.6) | 3.23(30.0) |
| | Phosphorus-containing acid ester *2 | 0.2 | 60 | 47.3 | 4.82(45.0) | 3.53(32.9) |

*1 Composition: $Na_5R'_5(P_3O_{10})_5$, wherein R' is 2-ethylhexyl, tradename Victor Wet 35B.
*2 Composition: $H_5R'_5(P_3O_{10})$, wherein R' is 2-ethylhexyl, tradename Victor Wet 35BH.
*3 The values are those of mol% based on converted peracid.

kept below 120°C, preferably in the range of from 60° to 100°C.

The method of this invention can be carried out both batchwise and continuously. Produced dihydric phenols can quite easily be separated from the reaction mixture after completion of the reaction. For example, the separation can easily be accomplished as by subjecting the reaction mixture in its unaltered form to rectification under reduced pressure.

The dihydric phenols which are produced by the method of this invention find various uses. Main uses are as follows:

| | Specific name of dihydric phenol | Use |
|---|---|---|
| 1. | Pyrocatechol | Intermediate for medicines and spicery |
| 2. | Hydroquinone | Photographic materials |
| 3. | Alkyl pyrocatechols | High molecular stabilizers |

Preferred embodiments of the present invention will be cited herein below, in conjunction with comparative examples, solely for the purpose of illustration. It should be understood that the present invention is not limited in any way to these examples.

As is clear from the results given in Table 1, the method of this invention can produce the product aimed at in higher yields than the conventional method.

EXAMPLE 2:

In the presence of 0.5% by weight of the same phosphoruscontaining acid ester as indicated in Example 1, 1 mol of phenol and 0.2 mol of peracetic acid were caused to react at 60°C. Consequently, there were produced 36.4% of pyrocatechol and 27.5% of hydroquinone respectively in terms of mol% based on converted peracetic acid, whose conversion was 99.1%.

EXAMPLE 3:

The procedure of Example 2 was repeated, except perisobutyric acid was used in place of peracetic acid. In the reaction, the conversion of perisobutyric acid was 99.7%. Consequently, there were produced 31.8% of pyrocatechol and 26.0% of hydroquinone respectively in terms of mol% of the converted perisobutyric acid.

EXAMPLE 4:

Five-neck flasks having a volume of 500 ml and provided with a stirrer, a reflux condenser, a sampling tube, a test specimen inlet and a thermometer were charged with 108.1g (1.0 mol) of paracresol and a different kind of peracid stabilizer as the catalyst shown in Table 1. Each flask was placed in a constant temperature bath kept at a temperature indicated in Table 1. Into the flask contents, 7.61g (0.1 mol) of peracetic acid in the form of about 35 weight% acetone solution was introduced through a micro-feeder over 20 minutes. Within 75 hours after the start of the addition of the peracetic acid, the contents of the flask were subjected to distillation under reduced pressure to obtain a fraction of 4-methyl-1,2-dihydroxybenzene having a boiling point of 124 - 125°C/6 mmHg. The results of this reaction are shown in the following table.

tert.-butyl phenol was 5.1%, that 4-tert.-butyl pyrocatechol was formed in a yield of 50% based on the converted butyl phenol and that the conversion of the peracetic acid was 95.2%.

Comparative Example 2:

The procedure of Comparative Example 1 was repeated, except phosphoric acid was added as a reaction catalyst in an amount corresponding to 1% by weight based on the amount of para-tert.-butyl phenol used. Consequently, the conversion of para-tert.-butyl phenol was 5.3%, 4-tert.-butyl pyrocatechol was formed in a yield of 52% based on the converted butyl phenol, and the conversion of peracetic acid was 96.0%.

Table 2

| Catalyst | | | | |
|---|---|---|---|---|
| Kind | Added amount (% by weight) | Reaction temperature (°C) | Conversion of peracetic acid (%) | 4-methyl-1,2-dihydroxybenzene produced (g) *4 |
| Comparative — | — | 60 | 92.5 | 4.65(40.5) |
| Present invention Pyridine-2,6-dimethanol | 0.2 | 100 | 94.1 | 6.92(59.3) |
| 8-Oxyquinoline | 1.0 | 60 | 95.8 | 6.19(52.1) |
| Dioctyl-dihydrogen-pyrophosphate | 0.1 | 60 | 98.7 | 8.06(65.8) |
| Phosphorus-containing acid ester *5 | 0.1 | 60 | 99.4 | 8.44(68.4) |

*4 The values are those of mol% based on the converted peracetic acid
*5 Composition: $Na_5R'_5(P_3O_{10})_2$, wherein R' is 2-ethylhexyl, tradename Victor Wet 35B.

EXAMPLE 5:

In the presence of 0.2% by weight of the same phosphorus-containing acid ester as indicated in Example 4, 1 mol or orthocresol and 0.2 mol of peracetic acid were caused to react at 50°C. Within 75 minutes after the start of the addition of peracid, the reaction product was analyzed by gas chromatography. Consequently, it was found that the conversion of peracetic acid was 99.8% and that there were produced 3-methyl-1,2-dihydroxy benzene and 2-methyl-1,4-dihydroxy benzene in amounts corresponding to 40.0% and 29.3% respectively.

EXAMPLE 6:

By repeating the procedure of Example 5, metacresol was subjected to reaction under the same conditions, except perisobutyric acid was used in place of peracetic acid. Consequently, the conversion of perisobutyric acid was 99.9% and there were obtained 10.3% of 3-methyl-1,2-dihydroxy benzene, 23.0% of 4-methyl-1,2-dihydroxy benzene and 25.9% of 3-metyl-1,4-dihydroxy benzene.

Comparative Example 1:

A five-neck flask having a volume of 500 ml and provided with a stirrer, a reflux condenser, a sampling tube, a test specimen inlet and a thermometer was charged with 75.1g (0.5 mol) of paratert.-butyl phenol and 20 ml of acetone as a solvent. The flask was placed in a constant temperture bath ketp at 60°C. Into the flask contents, 3.80g (0.05 mol) of peracetic acid in the form of about 35 weight% acetone solution was added through a micro-feeder over 12 minutes. Within 60 minutes after the start of the addition of peracid, the reaction solution was analyzed by gas chromatography. Consequently, it was found that the conversion of para-

EXAMPLE 7;

After the manner of the procedure of Comparative Example 1, the reaction was carried out by using 20 ml of ethyl acetate as a solvent for para-tert.-butyl phenol and 0.5% by weight of $Na_5R'_5$ $(P_3O_{10})_2$ (R' = 2-ethylhexyl, tradename "Victor Wet 35B") as a peracetic acid stabilizer based on the amount of butyl phenol used. Consequently, the conversion of parta-tert.-butyl phenol was 7.2%, 4-tert.-butyl pyrocatechol was formed in a yield of 77% based on the converted butyl phenol and the conversion of peracetic acid was 98.5%.

EXAMPLE 8:

The procedure of Example 7 was followed, except 103.2g (0.5 mol) of para-tert.-octyl phenol was used in place of para-tert.-butyl phenol and the reaction was carried out in a constant temperature bath kept at 80°C. Consequently, the conversion of para-tert.-octyl phenol was 7.3%, 4-tert.-octyl pyrocatechol was formed in a yield of 75% based on the converted octyl phenol, and the conversion of peracetic acid was 98.9%.

EXAMPLE 9:

The procedure of Example 8 was followed, except 20 ml of acetone was added as a solvent for para-tert.-octyl phenol and 4.5g (0.05 mol) of perpropionic acid in the form of about 25 weight% acetone solution was added over 20 minutes in place of peracetic acid. Consequently, the conversion of para-tert.-octyl phenol was 6.8%, 4-tert.-octyl pyrocatechol was formed in a yield of 61% based on the converted octyl phenol and the conversion of perpropionic acid was 100%.

EXAMPLE 10:

The procedure of Example 9 was repeated, except 10.4g (0.1 mol) of perisobutyric acid in the form of about 20 weight% acetone solution was added over 30 minutes in place of perpropionic acid. Consequently, the conversion of para-tert.-octyl phenol was 13.2%, 4-tert.-octyl pyrocatechol was formed in a yield of 58% based on the converted octyl phenol and the conversion of perisobutyric acid was 100%.

EXAMPLE 11:

The procedure of Example 7 was repeated, except 0.2% by weight of dioctyl pyrophosphate was used in place of $Na_5R'_5(P_3O_{10})_2$. Consequently, the conversion of para-tert.-butyl phenol was 7.2%, 4-tert.-butyl pyrocatechol was formed in a yield of 75% based on the converted butyl phenol and the conversion of peracetate was 99.0%.

EXAMPLE 12:

The procedure of Example 9 was repeated, except 0.2% by weight of pyridine-2,6-dimethanol was used as a catalyst and the reaction was carried out at 50°C. Consequently, the conversion of para-tert.-octyl phenol was 6.2%, 4-tert.-octyl pyrocatechol was formed in a yield of 54% based on the converted octyl phenol and the conversion of perpropionic acid was 97.2%.

EXAMPLE 13:

Five-neck flasks having a volume of 500 ml and provided with a stirrer, a reflux condenser, a sampling tube a peracetic acid inlet and a thermometer were charged with 94.0g of phenol and 0.20g of a different kind of catalyst indicated in Table 3 and heated to 60°C. To the contents of the flasks, 7.6g of peracetic acid dissolved in a mixed solvent of acetone and methyl acetate (mixing ratio of about 9 : 1 by volume) to a concentration of about 25% by weight was introduced dropwise over about 10 minutes, with the reaction temperature maintained at 60°C. Within two hours after the start of said addition, the reaction solutions were analyzed to determine the conversion of peracetic acid by iodometry and the conversion of phenol and the formation of dihydroxy phenols by gas chromatography, with the selectivity of dihydric phenols' production calculated on the basis of peracetic acid and phenol. The results are shown in Table 3. The analysis of the formed reaction products was performed by means of gas chromatography using Silicon DC-550 (carried in an amount of 20% by weight on a carrier: 40-60 mesh silane-treated Chromosolve W) as a filler.

Table 3

| Catalyst | Conversion of peracetic acid (%) | Conversion of phenol (%) | Dihydric phenyl produced (g) | | Selectivity of dihydric phenol formed (%) | |
|---|---|---|---|---|---|---|
| | | | Pyrocatechol | Hydroquinone | Based on peracid | Based on phenol |
| Comparative     None | 85.2 | 9.63 | 0.30 | 0.31 | 6.44 | 7.00 |
| Present invention | | | | | | |
| Iminodiacetic acid | 96.8 | 9.22 | 4.97 | 2.79 | 72.8 | 76.4 |
| Nitrylotriacetic acid | 95.2 | 7.32 | 5.08 | 3.28 | 79.6 | 100 |
| Ethylenediamine tetraacetic acid | 96.8 | 8.07 | 5.02 | 3.24 | 77.6 | 93.0 |
| Sodium ethylenediamine tetraacetate | 98.6 | 8.57 | 4.75 | 3.20 | 73.1 | 84.1 |
| Potassium ethylenediamine tetraacetate | 97.3 | 8.81 | 4.83 | 3.32 | 71.6 | 84.0 |
| Magnesium ethylenediamine tetraacetate | 96.5 | 8.11 | 5.37 | 3.11 | 79.8 | 94.9 |
| 1,2-Cyclohexanediamine tetraacetic acid | 98.1 | 10.12 | 5.21 | 2.87 | 74.8 | 72.5 |
| Diethylenetriamine pentaacetic acid | 96.9 | 8.62 | 5.06 | 3.36 | 78.8 | 88.5 |
| Citric acid | 81.3 | 6.18 | 2.42 | 0.94 | 37.5 | 49.3 |
| Tartaric acid | 82.0 | 6.07 | 2.71 | 0.88 | 39.1 | 53.7 |
| Monobasic sodium phosphate | 96.3 | 7.01 | 4.70 | 2.90 | 71.7 | 98.6 |
| Dibasic sodium phosphate | 98.8 | 7.12 | 4.53 | 2.80 | 67.1 | 93.2 |
| Dibasic potassium phosphate | 99.6 | 7.05 | 3.88 | 2.90 | 61.9 | 87.5 |
| Sodium pyrophosphate | 100 | 8.79 | 5.35 | 2.99 | 75.7 | 86.1 |

EXAMPLE 14:

The procedure of Example 13 was followed, except peracetic acid prepared in the form of 25 weight% ethyl acetate solution was used in amounts of 0.2 mol or 0.3 mol. The results are shown in Table 4.

Table 4

| Catalyst | Ethylenediamine tetraacetic acid | 1,2-Cyclohexane diamine tetraacetic acid | Ethylene diamine tetraacetic acid |
|---|---|---|---|
| Molarity of acetic acid used | 0.2 | 0.2 | 0.2 |
| Conversion of peracetic acid (%) | 95.0 | 95.6 | 94.7 |
| Conversion of phenol (%) | 14.9 | 14.7 | 20.4 |
| Yield of pyrocatechol (g) | 8.55 | 8.60 | 10.6 |
| Yield of hydroquinone (g) | 5.85 | 5.77 | 6.62 |
| Selectivity     Based on | | | |

Table 4-continued

| Catalyst | | Ethylene-diamine tetraacetic acid | 1,2-Cyclohexane diamine tetraacetic acid | Ethylene diamine tetraacetic acid |
|---|---|---|---|---|
| of dihydric phenol formed (%) | peracetic acid | 69.0 | 68.4 | 55.0 |
| | Based on phenol | 87.7 | 88.7 | 76.5 |

EXAMPLE 15:

Five-neck flasks having a volume of 500 ml and provided with a stirrer, a reflux condenser, a sampling tube, a peracetic acid inlet and a thermometer were charged with 50.0g of para-tert.-butyl phenol, 50g of toluene as a solvent therefor, and 0.20g of a different kind of catalyst shown in Table 5. To the flask contents, 19.9g of peracetic acid dissolved to a concentration of 25.4 weight% in the same peracetic acid solvent as used in Example 13 was introduced over 10 minutes. Within one hour after the start of the introduction, the reaction solutions were analyzed for conversion of peracetic acid, conversion of para-tert.-butyl phenol, yield of 4-tert.-butyl pyrocatechol, and selectivity of pyrocatechol production based on peracetic acid and phenol. The results are shown in Table 5.

Table 5

| | | Comparative example | This invention | | |
|---|---|---|---|---|---|
| Reaction catalyst | | None | Ethylene-diamine tetraacetic acid | Diethylene-triamine pentaacetic acid | Nitrilo-triacetic acid |
| Conversion of peracetic acid (%) | | 96.4 | 97.4 | 97.8 | 95.8 |
| Conversion of para-tert.-butyl phenol (%) | | 13.2 | 9.94 | 13.4 | 13.4 |
| 4-tert.-butyl pyrocatechol formed (g) | | 0.29 | 2.71 | 4.45 | 0.5 |
| Selectivity of 4-tert.-butyl pyrocatechol formed (%) | Based on peracetic acid | 2.72 | 25.1 | 41.0 | 4.38 |
| | Based on phenol | 3.96 | 49.2 | 59.7 | 6.26 |

EXAMPLE 16:

The procedure of Example 15 was followed, except 90.0g of paratert.-octyl phenol was used in place of para-tert.-butyl phenol, 30g of toluene was used as a solvent therefor and the oxidation was carried out by a solution having 3.30g of peracetic acid dissolved in the same solvent as used in Example 1 to a concentration of about 25 weight%. The results are shown in Table 6.

Table 6

| | Comparative example | This invention | | |
|---|---|---|---|---|
| Reaction catalyst | None | Ethylene-diamine tetraacetic acid | Diethylene-triamine pentaacetic acid | Nitrilo-triacetic acid |
| Conversion of peracetic acid (%) | 98.6 | 99.1 | 99.0 | 98.7 |
| Conversion of para-tert.-butyl phenol (%) | 7.01 | 9.37 | 7.60 | 9.52 |
| 4-tert.-octyl pyrocatechol formed(g) | 2.05 | 5.60 | 5.67 | 3.70 |
| Selectivity of 4-tert.-butyl pyrocatechol formed (%) Based on peracetic acid | 21.5 | 58.2 | 59.3 | 38.7 |
| Based on phenol | 30.4 | 61.5 | 78.2 | 40.1 |

EXAMPLE 17:

The procedure of Example 13 was repeated, except 1,2-cyclohexanediamine tetraacetic acid was used as a reaction catalyst and the reaction was performed by using 52.0g of a solution having perisobutyric acid, in place of peracetic acid, dissolved in acetone to a concentration of 20 weight%. Consequently, the conversion of perisobutyric acid was 99.5%, the coversion of phenol was 8.00%, the yield of pyrocatechol was 4.30g, the yield of hydroquinone was 2.82g and the selectivity of dihydric phenol formed was 65.0% based on peracetic acid and 80.8% based on phenol.

EXAMPLE 18:

Five-neck flasks having a volume of 500 ml and provided with a stirrer, a reflux condenser, a sample collecting tube, a peracid inlet and a thermometer were charged with 1 mol of anisole and 0.2% by weight, based on anisole in use, of a different kind of catalyst shown in Table 7. Each flask was heated to 80°C and 0.1 mol (used as 30% acetone solution) of peracetic acid was introduced dropwise into the contents of the flask over about 20 minutes. Within three hours after the start of the introduction, the reaction solution was analyzed for conversion of peracetic acid by the titration method and for conversion of anisole and yields of methylether products of dihydric phenols by gas chromatography using as a filler silicon DC-550 (carried in an amount of 20% by weight on a carrier, 40 – 60 mesh silane-treated Chromosolv W). The results are shown in Table 7.

Table 7

| Reaction catalyst | Conversion of peracetic acid | Conversion of anisole (%) | Dihydric phenol monomethylethers formed (g) | |
|---|---|---|---|---|
| | | | Pyrocatechol monomethylether | Hydroquinone monomethylether |
| This invention | | | | |
| 8-Oxyquinoline | 95.2 | 6.40 | 2.80 | 1.35 |
| Pyridine-2,6-dimethanol | 94.2 | 5.01 | 2.86 | 1.43 |
| Dioctyl-dihydrogen-pyrophosphate | 98.9 | 5.82 | 3.81 | 1.84 |
| Phosphorus-containing ester* | 99.2 | 5.22 | 3.29 | 1.65 |
| Sodium pyrophosphate | 98.7 | 6.13 | 3.50 | 1.89 |
| Ethylenediamine | 97.6 | 6.32 | 3.78 | 1.88 |
| Diethylenetriamine pentaacetic acid | 98.0 | 6.21 | 3.71 | 1.95 |
| Comparative example | | | | |
| None | 94.0 | 6.20 | 2.19 | 1.10 |

*Composition $Na_5R'_5(P_3O_{10})_2$, R' 2-ethyl-hexyl, tradename Victor Wet 35B.

EXAMPLE 19:

The procedure of Example 18 was followed, except sodium ethylenediamine tetraacetate was used as a reaction catalyst and the oxidation was effect by using perpropionic acid (as 20% solution in ethyl acetate) in place of peracetic acid. Consequently, the conversion of peracid was 98.7%, the conversion of anisole was 7.62% and there were produced 3.40g of pyrocatechol monomethyl ether and 1.82g of hydroquinone monomethyl ether.

EXAMPLE 20:

The procedure of Example 18 was repeated, except Victor Wet 35B (phosphur-containing ester) was used as a reaction catalyst and 4-methyl anisole was used in place of anisole. Consequently, the conversion of peracetic acid was 96.2%, the conversion of 4-methyl anisole was 8.02% and there was formed 4.55g of 4-methyl-2-hydroxy anisole.

EXAMPLE 21:

The procedure of Example 18 was followed, except the reaction was carried out for two hours at 60°C using phenyl ethyl ether in place of 4-metyl anisole. Consequently, the conversion of peracetic acid was 65.1%, the conversion of phenyl ethyl ether was 5.97% and there were produced 3.51g of hydroquinone ethyl ether and 1.49g of pyrocatechol monoethyl ether.

EXAMPLE 22:

The procedure of Example 21 was repeated, except diphenyl ether was used in place of 4-methyl anisole and perisobutyric acid (used as 20% acetone solution) was used in place of peracetic acid. Consequently, the conversion of perisobutyric acid was 98.5%, the conversion of diphenyl ether was 8.28% and there were produced 4.15g of 2-hydroxydiphenyl ether and 2.04g of 4-hydroxydiphenyl ether.

EXAMPLE 23:

Five-neck flasks having a volume of 500 ml and provided with a stirrer, a reflux condenser, a sampling tube a peracetic acid inlet and a thermometer were charged with 94.0g of phenol and a different kind of catalyst indicated in Table 8 and heated to 60°C ~ 65°C. To the contents of the flasks, 7.6g of peracetic acid dissolved in a mixed solvent of acetone and methyl acetate (mixing ratio of about 9 : 1 by volume) to a concentration of about 18 ~ 30% by weight was introduced dropwise over about 10 minutes, with the reaction temperature maintained at 60°C ~ 65°C. Within two hours after the start of said addition, the reaction solutions were analyzed to determine the conversion of peracetic acid by iodometry and the conversion of phenol and the formation of dihydroxy phenols by gas chromatography, with the selectivity of dihydric phenols' production calculated on the basis of peracetic acid and phenol. The results are shown in Table 8. The analysis of the formed reaction products was performed by means of gas chromatography using Silicon DC-550 (carried in an amount of 20% by weight on a carrier: 40-60 mesh silane-treated Chromosolve W) as a filler.

Table 8

| | Catalyst | | Peracetic acid | | Conversion of phenol (%) | Dihydric phenol produced (g) | | Selectivity of dihydric phenol formed (%) | |
|---|---|---|---|---|---|---|---|---|---|
| | Kind | Weight (g) | Concentration (wt %) | Conversion (%) | | Pyrocatechol | Hydroquinone | Based on peracid | Based on phenol |
| This invention | Dimethyl phosphate | 0.1 | | | | | | | |
| | Monomethyl " | 0.1 | 25.6 | 97.7 | 8.3 | 5.4 | 3.6 | 83.3 | 98.0 |
| | Dimethyl " | 0.15 | 18.4 | 96.4 | 7.8 | 5.3 | 3.2 | 80.2 | 99.1 |
| | Monomethyl " | 0.3 | 29.8 | 98.6 | 8.0 | 5.1 | 3.3 | 77.4 | 95.5 |
| | Diethyl " | 0.2 | 24.5 | 90.2 | 7.8 | 2.1 | 1.8 | 39.3 | 45.4 |
| | Di-normal-butyl " | 0.2 | 25.1 | 85.6 | 7.5 | 1.8 | 1.6 | 35.6 | 40.6 |
| | Monomethyl pyrophosphate | 0.1 | 25.1 | 88.1 | 7.5 | 3.2 | 2.4 | 57.8 | 67.9 |
| | Tripropyl pyrophosphate | 0.5 | 25.5 | 96.2 | 8.2 | 3.8 | 2.7 | 61.4 | 72.1 |
| | Dihexyl pyrophosphate | 0.2 | 25.1 | 98.8 | 8.2 | 5.4 | 3.5 | 81.9 | 98.7 |
| Comparative example | None | — | 25.0 | 85.2 | 9.6 | 0.3 | 0.3 | 6.4 | 7.0 |
| | Trimethyl phosphate | 0.2 | 22.8 | 81.8 | 7.0 | 1.5 | 0.7 | 24.4 | 28.6 |
| | Triethyl phosphate | 0.2 | 25.5 | 86.1 | 9.3 | 0.6 | 0.4 | 10.6 | 9.8 |

EXAMPLE 24:

The procedure of Example 23 was repeated, except 75.1g of para-tert.-butyl phenol dissolved in 20 ml of acetone was introduced in the flask in place of phenol. To the solution, 0.1g of diethyl-dihydrogen-pyrrolic acid ester was added and then 3.8g (0.05 mol) of peracetic acid in the form of an acetone solution containing the peracetic acid by about 35 percent by weight was added dropwise over a period of 12 minutes. At the end of 60 minutes following the start of the dropwise introduction of said acid, the reaction solution was analyzed by following the procedure of Example 23. The analysis showed that 4-tert.-butyl pyrocatechol was formed at a selectivity of 69 mol percent based on the converted para-tert.-butyl phenol, with the conversion of peracetic acid at 95.2 percent and that of para-tert.-butyl phenol at 6.2 percent respectively. When this reaction was performed in the absence of the catalyst, the conversion of butyl phenol was 5.1 percent and the selectivity of catechol was 50 mol percent, although the conversion of peracetic acid was substantially the same.

EXAMPLE 25:

The procedure of Example 23 was repeated, except 1 mol of anisole was used in place of phenol. To the solution in the flask, 0.2g of a mixture of dimethyl phosphate and monomethyl phosphate (available on the market under the designation of "dimethyl phosphate" and containing about 50 percent of dimethyl phosphate, the remainder being monomethyl phosphate) was added and heated to 80°C. Then 0.1 of perpropionic acid (prepared in the form of 30 percent ethyl acetic acid solution) was introduced dropwise over a period of about 20 minutes. At the end of three hours following the start of said dropwise introduction of acid solution, the reaction solution was analyzed by repeating the procedure of Example 23. The analysis showed that 2.85g of pyrocatechol monomethyl ether and 1.44g of hydroquinone monomethyl ether were produced, with the conversion of perpropionic acid at 99.1 percent and that of anisole at 6.0 percent. When this reaction was performed in the absence of the catalyst, the yield of pyrocatechol monomethyl ether was 2.01g and that of hydroquinone monomethyl ether was 1.00g, although the conversion of each of the reactants was substantially the same.

What is claimed is:

1. A method for the manufacture of dihydric phenols by the oxidation of monohydric phenols of the generic formula:

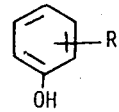

wherein, R is one member selected from the group consisting of H and alkyls having 1–12 carbon atoms, said oxidation being carried out at a temperature in the range of from 50°C to 150°C with one organic peracid selected from the group consisting of peracetic acid, perpropionic acid and perisobutyric acid in the presence of at least one member selected from the group consisting of:
  pyridine-2,6-dimethanol,
  8-oxyquinoline,
  $Na_5R'_5(P_3O_{10})_2$ wherein R' is one member selected from the group consisting of alkyls having 4 - 10 carbon atoms,
  $H_5R'_5(P_3O_{10})_2$ wherein R' is one member selected from the group consisting of alkyls having 4 - 10 carbon atoms,
  polycarboxylic acids containing 1-3 nitrogen atoms and having a heavy metal ion-chelating property selected from the group consisting of iminodiacetic acid, nitrylotriacetic acid, ethylenediaminotetracetic acid, 1,2-cyclohexandiamine tetracetic acid and diethylenetriamine pentacetic acid,
  magnesium salts of said polycarboxylic acids,
  sodium salts of said polycarboxylic acids,
  potassium salts of said polycarboxylic acids,
  polycarboxylic acids containing 1-3 OH radicals and having a heavy metal ion-chelating property selected from the group consisting of citric acid and tartaric acid,
  magnesium salts of said polycarboxylic acids,
  sodium salts of said polycarboxylic acids,
  sodium salt of phosphoric acid,
  potassium salt of phosphoric acid,
  mono and di-alkyl esters of phosphoric acid, having 12 or less carbon atoms,
  sodium salt of pyrophosphoric acid, and mono, di and tri-alkyl esters of pyrophosphoric acid, having 12 or less carbon atoms.

2. A method according to claim 1, wherein the oxidation is carried out at 50°C – 100°C, using the organic peracid in an amount of 0.1 – 0.5 mol per mole of monohydric phenol and the catalyst in an amount of 0.05 – 1% by weight based on monohydric phenol.

3. A method according to claim 1, wherein R of the monohydric phenol represented by the generic formula:

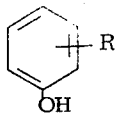

is an alkyl group having 2 to 12 carbon atoms.

4. A method for the manufacture of dihydric phenols by the oxidation of monohydric phenols of the generic formula:

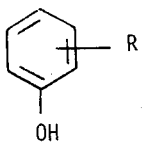

wherein R is one member selected from the group consistng of H and alkyls having 1-12 carbon atoms, said oxidation being carried out at a temperature in the range of from 50°C to 100°C with one organic peracid selected from the group consisting of peracetic acid, perpropionic acid and perisobutyric acid in an amount of 0.1 – 0.5 mol per mole of phenol, in the presence of at least one member, in an amount of 0.05 – 1% by weight based on phenol, selected from the group consisting of:
pyridine-2,6-dimethanol,
8-oxyquinoline,
$Na_5R'_5(P_3O_{10})_2$ wherein R' is one member selected from the group consisting of alkyls having 4-10 carbon atoms,
$H_5R'_5(P_3O_{10})_2$ wherein R' is one member selected from the group consisting of alkyls having 4-10 carbon atoms,
polycarboxylic acids containing 1-3 nitrogen atoms and having a heavy metal ion-chelating property selected from the group consisting of iminodiacetic acid, nitrylotriacetic acid, ethylenediaminotetracetic acid, 1,2-cyclohexandiamine tetracetic acid and diethylenetriamine pentacetic acid,
magnesium salts of said polycarboxylic acids,
sodium salts of said polycarboxylic acids,
potassium salts of said polycarboxylic acids,
polycarboxylic acids containing 1-3 OH radicals and having a heavy metal ion-chelating property, selected from the group consisting of citric acid and tartaric acid,
magnesium salts of said polycarboxylic acids,
sodium salts of said polycarboxylic acids,
sodium salt of phosphoric acid,
potassium salt of phosphoric acid,
mono- and di-alkyl esters of phosphoric acid having 12 or less carbon atoms,
sodium salt of pyrophosphoric acid, and
mono-, di- and tri-alkyl esters of pyrophosphoric acid having 12 or less carbon atoms.

5. A method according to claim 4, wherein said monohydric phenol represented by the generic formula:

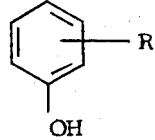

is one member selected from the group consisting of cresol and phenol.

6. A method according to claim 4, wherein R is selected from the group consisting of alkyl as having 2 – 12 carbon atoms.

* * * * *